United States Patent [19]
Hebgen et al.

[11] Patent Number: 4,720,599
[45] Date of Patent: Jan. 19, 1988

[54] PREPARATION OF VINYL CHLORIDE BY THERMAL CRACKING OF 1,2-DICHLOROETHANE

[75] Inventors: Werner Hebgen, Nussloch; Eckehard Danz, Ludwigshafen; Gerd Krome, Weisenheim; Erhard Stahnecker, Heidelberg, all of Fed. Rep. of Germany

[73] Assignee: BASF Aktiengesellschaft, Ludwigshafen, Fed. Rep. of Germany

[21] Appl. No.: 658,464

[22] Filed: Oct. 9, 1984

Related U.S. Application Data

[63] Continuation of Ser. No. 424,876, Sep. 27, 1982, abandoned.

[30] Foreign Application Priority Data

Oct. 15, 1981 [DE] Fed. Rep. of Germany ....... 3140892

[51] Int. Cl.$^4$ .............................................. C07C 17/34
[52] U.S. Cl. ................................................... 570/226
[58] Field of Search ................................. 570/226, 227

[56] References Cited

U.S. PATENT DOCUMENTS 3,476,955 11/1969 Krekeler et al. ................... 570/238
3,761,361 9/1973 Wall .................................... 570/226
3,903,182 9/1975 Rechmeier et al. ................. 570/226

Primary Examiner—Donald B. Moyer
Assistant Examiner—Joseph A. Boska
Attorney, Agent, or Firm—Keil & Weinkauf

[57] ABSTRACT

A process for the preparation of vinyl chloride by vaporizing liquid 1,2-dichloroethane, thermally cracking the 1,2-dichloroethane and cooling the hot reaction mixture by means of cooled and condensed portions of the reaction mixture, wherein a defined amount of the 1,2-dichloroethane is taken off as liquid in or downstream of the vaporizer and mixed with a defined amount of the cooled liquid portion of the reaction mixture, the mixture is distilled and the constituents taken off the top of the distillation column are mixed with the liquid 1,2-dichloroethane upstream of the vaporizer while the constituents taken off the bottom of the distillation column are worked up by distillation.

2 Claims, 1 Drawing Figure

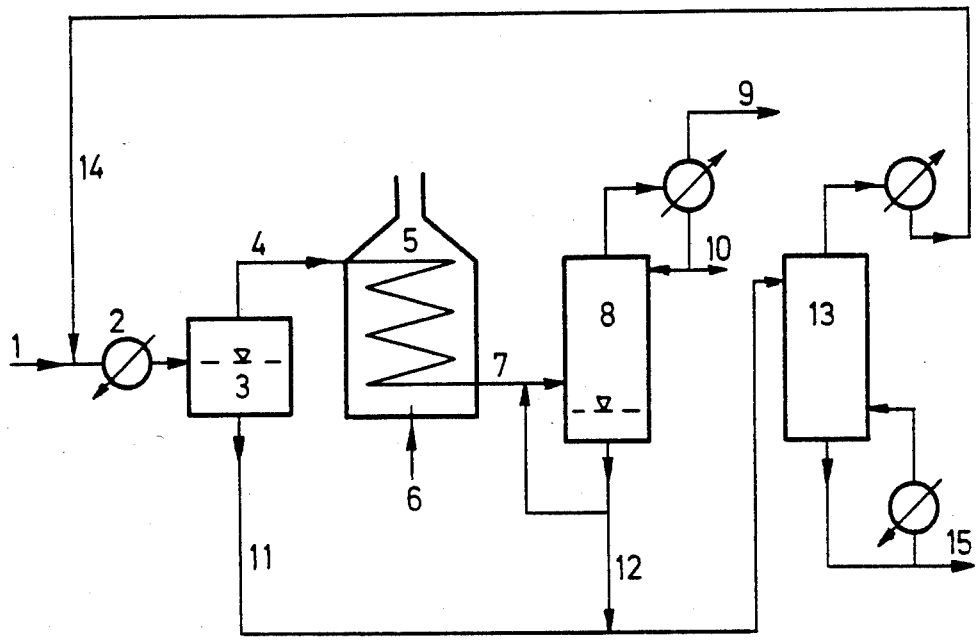

PREPARATION OF VINYL CHLORIDE BY THERMAL CRACKING OF 1,2-DICHLOROETHANE

This application is a continuation of application Ser. No. 424,876 filed on Sept. 27, 1982, abandoned.

The present invention relates to a process for the preparation of vinyl chloride by vaporizing liquid 1,2-dichloroethane, thermally cracking the latter, cooling the hot reaction products and then separating them by distillation.

Vinyl chloride is produced industrially by thermal cracking of 1,2-dichloroethane. For this purpose, pure 1,2-dichloroethane is vaporized and thermally cracked, preferably at from 480° to 520° C. The hot reaction products are cooled by a quenching stage employing direct cooling, wherein the removal of heat results in total or partial condensation, and are then subjected to further working up. In the quenching stage, a proportion of the cooled liquid constituents is added to the hot reaction product, so that after the excess heat has been removed condensation of the high-boiling constituents occurs. To separate the reaction product, hydrogen chloride is first removed and, in a second distillation unit, further distillative separation is effected into pure vinyl chloride, residual 1,2-dichloroethane and low-boiling and high-boiling constituents. On vaporization of 1,2-dichloroethane, incomplete pyrolysis thereof and subsequent cooling (quenching), residues in the form of high-boiling constituents and even solid materials (soot and coke) are formed. These constituents must be discharged from the system. The material taken off the quenching stage for discharging (and predominantly containing 1,2-dichloroethane, with up to 5% of vinyl chloride and up to 1% of HCL) is in the main concentrated under reduced pressure, and under these conditions it is unavoidable that small amounts of 1,2-dichloroethane cannot be separated from the high-boilers and solid products and accordingly are lost. The volatile constituents, namely vinyl chloride and hydrogen chloride, can only be recovered at considerable expense and in general are discharged with the flue gas.

It is an object of the present invention to modify a process of the above type for the preparation of vinyl chloride by vaporization and thermal cracking of 1,2-dichloroethane in such a way that losses of useful products are reduced.

We have found that this object is achieved, according to the invention, by a process wherein from 1 to 10% by weight of the liquid 1,2-dichloroethane are taken off in or downstream of the vaporizer and mixed with a cooled liquid portion of the reaction products, amounting to from 5 to 15% by weight of the reaction mixture, and this mixture is worked up by distillation.

In a preferred embodiment of the process, the constituents taken off the top of the distillation column are mixed with the liquid 1,2-dichloroethane before vaporization whilst the constituents taken off the bottom of the distillation column are worked up by further distillation.

We have found, surprisingly, that the constituents which are taken off the top of the distillation column and essentially contain 1,2-dichloroethane and smaller amounts of hydrogen chloride and vinyl chloride, as well as other low-boiling components, can be mixed with the liquid 1,2-dichloroethane and subsequently be vaporized without interfering with the course of the thermal cracking process. Moreover, we have found that in the process sequence according to the invention the production of insoluble and high-boiling constituents is reduced. The process is illustrated in the FIGURE. Pure 1,2-dichloroethane (1) is mixed with the mixture, consisting predominantly of 1,2-dichloroethane, hydrogen chloride and vinyl chloride, which has been taken off the top of the column (13), and the resulting mixture is substantially vaporized in the vaporizer (2). In the phase separation vessel (3), which can be integral with the vaporizer, a gaseous phase and a liquid phase form. The gaseous phase (4) is fed to the cracking furnace (5), in which the incomplete cracking of 1,2-dichloroethane into vinyl chloride and hydrogen chloride occurs. The furnace is fired with a mixture of air and fuel (6). Cracking occurs at preferably from 480° to 540° C. The hot reaction mixture (7) is mixed with liquid constituents which are taken off the bottom of the column (8) (quenching stage), and the mixture is fed to the column (8). The bottom constituents, which are at from 140° to 200° C., are admixed in such amounts that the resulting mixture enters the column (8) at about the boiling point. At the top of the column, the gaseous and liquid constituents are taken off after partial or complete condensation and the streams (9) and (10) are subjected to further separation into vinyl chloride, hydrogen chloride and 1,2-dichloroethane. From 1 to 10% by weight of the feed to the vaporizer (2) are taken off as liquid (11) from the separating vessel (3) and mixed with the high-boilers and solid residues (12) taken off the bottom of the column (8). The stream (12) amounts to 5-15% by weight of the stream (7). The resulting mixture is fed to the column (13), where the stream (14) is taken off at the top and fed into the stream (1) upstream of the vaporizer. The stream (14) amounts to 5-30% of the pure 1,2-dichloroethane (1). At the bottom of the column (13), the bottom discharge material (15) is taken off together with the solid products formed and the high-boiling constituents, and worked up by distillation.

It is however also possible to work up the stream (14) conjointly with the streams (9) and (10) by distillation. The advantage of the embodiment in which the stream (14) is added to the stream (1) is a saving of energy in working-up.

As explained above, the advantage of the process according to the invention is that the useful products such as vinyl chloride and hydrogen chloride which are contained in (12) are recovered in column (13) and are recycled, in the stream (14), to the reaction as a mixture with the 1,2-dichloroethane originating from steam (11).

EXAMPLE

The process sequence followed is as illustrated in the FIGURE.

8.5 t/h of stream (14) are admixed to 59 t/h of pure (99%) 1,2-dichloroethane (1). 64.5 t/h of the mixture are vaporized (4) and fed to the cracking furnace (5). The reaction mixture (7), which is at 450°-500° C. and a pressure of 15 bar, is quenched with liquid constituents from the column (8). From column (8), 58.5 t/h, as streams (9) and (10), are passed to the stage where the material is worked up for vinyl chloride. 6 t/h of stream (12), which contains 3% of vinyl chloride and 0.5% of hydrogen chloride, are mixed with 3 t/h of stream (11) and this mixture is fed to column (13), operated under a pressure of 1.2 bar. 8.5 t/h are taken off at the top and condensed at 85° C. This stream (14) is mixed with the stream (1) upstream of the vaporization stage (2). The material taken off the bottom of the column (13) in amounts of 0.5 t/h contains all high-boiling and solid constituents. Their proportion amounts to 0.5%, based on 1,2-dichloroethane (1) introduced.

If, instead of the method according to the invention, the conventional method is followed, the proportion of high-boiling and solid constituents is 2%.

We claim:

1. A process for the preparation of vinyl chloride comprising the steps of:

(a) vaporizing liquid 1,2-dichloroethane,
   (b) thermally cracking the 1,2-dichloroethane vapor,
   (c) cooling the hot reaction mixture which is under pressure by quenching, and
   (d) separating the reaction mixture by distillation, wherein from 1 to 10% by weight of the liquid 1,2-dichloroethane is taken off in or downstream of the vaporizer and mixed with 5 to 15% by weight of the cooled liquid portion of the reaction mixture from the quenching stage (c), the mixture of the liquid 1,2-dichloroethane and the said cooled liquid portion thereafter being worked up by distillation.

2. A process as set forth in claim 1, wherein the constituents taken off the top of the distillation column amount to 5–30% of the liquid 1,2-dichloroethane and are fed to the stream of the liquid 1,2-dichloroethane before vaporization.

* * * * *